United States Patent [19]

Ikushima et al.

[11] Patent Number: 5,869,548
[45] Date of Patent: Feb. 9, 1999

[54] DENTAL MATERIAL

[75] Inventors: Keisuke Ikushima, Tokyo; Akira Hasegawa, Aichi, both of Japan

[73] Assignee: GC Dental Products Corporation, Aichi, Japan

[21] Appl. No.: 845,906

[22] Filed: Apr. 28, 1997

[51] Int. Cl.$^6$ .................................. C08K 3/34; A61K 6/08
[52] U.S. Cl. .................... 523/116; 523/115; 524/264; 524/176; 524/443; 524/450; 501/81; 501/66; 501/68
[58] Field of Search ...................................... 523/115, 116; 524/443, 450, 264, 176; 501/81

[56] References Cited

U.S. PATENT DOCUMENTS

| | | | |
|---|---|---|---|
| 4,314,380 | 2/1982 | Miyata et al. ............................ | 623/16 |
| 4,375,967 | 3/1983 | Schaefer .................................. | 524/450 |
| 4,381,918 | 5/1983 | Ehrnford .................................. | 523/115 |
| 4,412,015 | 10/1983 | Lustgarten et al. ..................... | 524/450 |
| 5,676,745 | 10/1997 | Kelly et al. .............................. | 424/423 |

*Primary Examiner*—Andrew E. C. Merriam
*Attorney, Agent, or Firm*—Wenderoth, Lind & Ponack, L.L.P.

[57] ABSTRACT

A dental material comprising a porous ceramics formed into an artificial tooth, an inlay, an onlay, a crown, a crown bridge or into a block shape suitable for CAD/CAM, sintered, having communicating holes, and impregnated with a resin. A porous ceramics formed from a network-forming oxide is applicable, and an intermediate oxide and a network-modifying oxide may also be adopted. The porous ceramics should preferably have a porosity within a range of from 0.5 to 70%. The resin should preferably a polymer of a monomer and/or oligomer containing at least an ethylenic double bond. Prior to impregnation of the porous ceramics with the resin, the porous ceramics should preferably be subjected to a coupling treatment.

26 Claims, 1 Drawing Sheet

Fig. 1

DENTAL MATERIAL

BACKGROUND OF THE INVENTION

1. Field of the invention

The present invention relates to a dental material. More particularly, the present invention relates to a composite dental material which is useful as an artificial tooth, an inlay, an onlay, a crown, a crown bridge and the like.

2. Description of the prior art

A dental material is generally required to satisfy various requirements such as sound mechanical strength and machinability, a low cost, an excellent aesthetic merit, absence of biological detrimentality and a good biological affinity. Various dental materials including resins, composite materials formed by dispersing an inorganic substance in a resin, ceramic materials, amalgams, and alloys of precious and base metals have been developed are now practically applied.

Various resins for dental purposes comprising methacrylate copolymers mainly consisting of methylmethacrylate have been developed and are in use as dental resins. These resins, being excellent in aesthetic merit, color fastness and impact resistance, are low in mechanical strength such as wear resistance and bending strength. The occlusion force during mastication of food, varying between different persons, is believed to be 78 kg on the average, and this occlusion force causes a huge stress on the tip of teeth. For these reasons, a resin as used as a dental material is defective in that is suffers from a considerable wear resulting from mastication over a long period of time, and deformation is easily caused by occlusion.

With a view to overcoming the defects of resins as described above, a composite resin made by mixing and dispersing an inorganic substance in a methacrylate-based copolymer resin has been developed. This material is advantageous in that it has a satisfactory aesthetic merit necessary for the foreteeth, and has an improved mechanical strength over a material made from a resin alone even in the molar segment required to have a mechanical strength sufficient to withstand occlusion. In order to improve physical properties of the composite resin such as mechanical strength and bending strength, and thus to achieve physical properties closer to those of natural teeth, it is necessary to uniformly disperse an inorganic substance throughout the resin, and to improve the filling ratio. The filling ratio can be improved with a resin having a large particle size. When such a resin is attached in the oral cavity as an artificial tooth, an inlay, an onlay, a crown or a crown bridge, however, the composite resin exhibits a rough surface, resulting in unavailability of a smooth and glossy surface, thus leaving a feeling of incompatibility in terms of touch with the palate. Furthermore, when the inorganic substance peels off the resin surface as a result of use for a long time and deposits accumulate at this portion, it is colored and this further reduces aesthetic merit. In the case of a composite resin having a small particle size, in contrast, as compared with those of a large particle size, the total surface area of the inorganic substance for the same volume increases, and along with the increase in viscosity upon dispersion of the inorganic substance in the resin, improvement of the filling ratio is limited to a certain level. At the same time, difficulties are encountered in handling and operability in manufacturing artificial teeth or forming or cutting clinically into an inlay, an onlay, a crown or a crown bridge. When using it in the form of ultra-fine powder, furthermore, weak electric charge of the particle surfaces and Van der Waars force cause easy cohesion of fine particles, making it difficult to obtain a uniform dispersion in the resin. Because coherent particles contain voids, there are difficulties in this case also in manufacturing artificial teeth or forming or cutting clinically into an inlay, an onlay, a crown or a crown bridge. Cohesion leads to a rough surface, leaving a feeling of incompatibility in touch with the palate. Trials are being made to solve the foregoing problems by combining different particle sizes, i.e., coarse and fine particles, charged in the resin so as to achieve presence of fine particles in the gaps between coarse particles. In terms of obtaining a uniform dispersion and a high filling ratio, a satisfactory result has not as yet been achieved. Under these circumstances, a composite resin having satisfactory mechanical strength, color fastness and coloring resistance for a long time has not as yet been obtained.

A porcelain material, which is a ceramic dental material used for long, is high in wear resistance and bending strength, excellent in aesthetic merit, color fastness and coloring resistance, free from biological detrimentality or irritation in the oral cavity, and is a stable dental material exhibiting no change in material quality even in a long-term use. As compared with a resin or a composite resin, however, it is defective in that it is high in cost, poor in elasticity, low in impact resistance because of brittleness, and tends to suffer cracking and fracture. In manufacturing a porcelain material, there occurs a considerable shrinkage caused by firing, thus making it difficult to accurately sinter into a prescribed shape. It is the usual practice to use a porcelain material after polishing and form-correction. Thermal stress during correction polishing causes microcracks which grow larger through repetition of daily occlusion pressure during mastication of food and impact caused by chewing hard food, thus resulting in fatigue breakage, or under an excessive occlusion load, in breakage. When a porcelain material is used as a ceramic tooth in a denture, mechanical holding means such as a pin or a retaining hole is provided in the ceramic tooth to achieve an integral connection of the porcelain material and the resin, because of a very low adhesion between the ceramic tooth and the resin serving as a plate or a support. Such holding means tends however to be subjected to stress concentration, and a defective attachment causes cracks in the surrounding resin or breakage of the ceramic tooth after attachment in the oral cavity. The ceramic tooth may also tend to come off the denture base of resin. For these reasons, manufacture of a satisfactory denture using a ceramic tooth requires skill and a high cost.

An amalgam and metallic materials including precious and base metals satisfying various requirements for physical properties are often kept at a distance for their poor aesthetic merit since they have metallic gloss, and some are eluted and exhibit toxicity, thus giving the risk of exerting an adverse effect on human health.

When any of these dental materials is used for dental therapy in the form of an artificial tooth, an inlay, an onlay, a crown or a crown bridge, it is necessary to use various machines and tools and conduct processing at an accuracy of at least 50 to 100 g m. Skill of a high degree is required until a person becomes capable of manually accomplish processing at such a high accuracy, and it is not easy to maintain accuracy at this level. In addition, it is difficult to conduct such process at a high efficiency, and this forms a cause of a high cost. For the purpose of solving the difficulty of keeping skilled operators, accomplishing processing rapidly at a high accuracy, and reducing the cost, it is now tried to integrally carry out all operations ranging from input of dental processing data, processing, design and to cutting and finish-processing of the dental material by the use of a CAD/CAM system, and there is an increasing demand for developing a dental material more suitable for the CAD/CAM system.

SUMMARY OF THE INVENTION

The present invention was created as a result of extensive studies carried out to develop a dental material capable of solving the foregoing defects of conventional dental materials including resins, composite resins, porcelain materials and metallic materials in view of the circumstances as described above, and has an object to provide an inexpensive dental material which can keep wear resistance, mechanical strength such as bending strength, color fastness, coloring resistance and aesthetic merit for a long period of time, and is excellent in modulus of bending elasticity and impact strength, and in addition, is suitable for a CAD/CAM system.

The foregoing and other objects, functions and effects of the present invention will become clear from the following detailed description and the drawings.

DETAILED DESCRIPTION OF PREFERRED EMBODIMENTS

The foregoing object is achieved by impregnating communicating holes of a porous ceramics with a resin. More specifically, the object is achieved by impregnating with a resin a porous ceramics obtained by forming into an artificial tooth, an inlay, an onlay, a crown or a crown bridge or into a block shape suitable for CAD/CAM, and then sintered.

That is, the dental material of the present invention comprises porous ceramics impregnated with a resin.

The porous ceramics should preferably be formed at least from a network-forming oxide, and more preferably, the porous ceramics should be formed from a combination of a network-forming oxide, an intermediate oxide and a network-modifying oxide.

The apparent porosity of the porous ceramics should preferably be within a range of from 0.5 to 70%.

The surface of the porous ceramics should preferably be coupling-treated with at least a coupling agent selected from the group consisting of a silane coupling agent, a titanate-based coupling agent and a zircoaluminate-based coupling agent. The resin should preferably have a polymer of a monomer and/or oligomer containing at least an ethylenic double bond.

The network-forming oxide should preferably be mainly $SiO_2$ or $B_2O_3$, $P_2O_5$, $Al_2O_3$, $ZrO_2$ or $Sb_2O_5$. Any of $Al_2O_3$, $ZrO_2$, BeO, $TiO_2$ and the like for the intermediate oxide, and any of CaO, $Na_2O$, $K_2O$, MgO, $Li_2O$, $CsO_2$, BaO, $La_2O_3$, $Y_2O_3$, ZnO and the like for the network-modifying oxide are appropriately selected and used in combination. Particularly, it is desirable for the manufacture of a porous ceramics to adopt one of aluminosilicate combinations $K_2O$—$Al_2O_3$—$SiO_2$ and $K_2O$—$Na_2O$—$Al_2O_3$—$SiO_2$, a borosilicate combination $Na_2O$—$B_2O_3$—$SiO_2$, and an alumino-borosilicate combination $Na_2O$—$Al_2O_3$—$B_2O_3$—$SiO_2$.

The individual contents in the foregoing combinations with $SiO_2$ as the main constituent should comprise, for the aluminosilicate combination $K_2O$—$Al_2O_3$—$SiO_2$, from 40 to 80 wt. % $SiO_2$, from 1 to 30 wt. % $K_2O$, and from 5 to 30 wt. % $Al_2O_3$; for the combination $K_2O$—$Na_2O$—$Al_2O_3$—$SiO_2$, from 40 to 80 wt. % $SiO_2$, from 1 to 30 wt. % $K_2O$, from 1 to 10 wt. % $Na_2O$, and from 5 to 30 wt. % $Al_2O_3$; for the borosilicate combination $Na_2O$—$B_2O_3$—$SiO_2$, from 60 to 95 wt. % $SiO_2$, from 0.1 to 10 wt. % $Na_2O$, and from 1 to 30 wt. % $B_2O_3$; and for the alumino-borosilicate combination $Na_2O$—$Al_2O_3$—$B_2O_3$—$SiO_2$, from 60 to 90 wt. % $SiO_2$, from 0.1 to 15 wt. % $Na_2O$, from 1 to 25 wt. % $Al_2O_3$ and from 1 to 20 wt. % $B_2O_3$. It is needless to mention that feldspar may partially be used to achieve the foregoing composition. Ceramics comprising crystal grains or ceramics containing crystal grains is also applicable. For exmple, a porous ceramics may be prepared by using a powder formed by causing precipitation of crystal grains through a heat treatment of a combination of any of the foregoing components.

To obtain a pore distribution permitting resin impregnation, these material should preferably have an average particle size within a range of from 3.0 to 50 µm or more preferably, from 5 to 30 µm. An average particle size of under 3.0 µm is not desirable since it leads to a lower porosity of the porous ceramics, a decreased number of communicating holes or small bores of communicating holes, more difficult impregnation of resin, and may cause a decrease in elasticity. If, however, even with an average particle size of under 3.0 µm, a porous ceramics is formed by appropriately selecting a binder, a forming pressure, a sintering temperature and a sintering time, or a low-viscosity one is adopted from among the compounds for resin described later, modulus of elasticity among physical properties of the resultant dental material may somewhat be reduced. However, because of other excellent properties including the surface condition, a fine powder having an average particle size of under 3.0 µm is applicable as a dental material. An average particle size of over 50 µm results in a poorer surface condition after resin impregnation and a lower wear resistance.

It is thus possible to appropriately select a particle size within a range not impairing mechanical strength such as wear resistance and bending strength, color fastness, coloring resistanse and aesthetic merit, although a difference in the particle size leads to some changes in mechanical properties and/or other conditions. For example, a porous ceramics having substantially satisfactory communicating holes can be formed by appropriately selecting a binder, a forming pressure, a sintering temperature and a sintering time, even from a raw material powder having an average particle size of over 50µm, only if the powder containing much particles having sizes of up to 150µm. Polymerization after penetration of the resultant porous ceramics through the communicating holes thereof with a compound for resin as described later can provide a product which, although slightly poor in the surface condition, is equal or even superior to the dental porcelain materials in elasticity and other properties and permits penetration of a high-viscosity compound for resin. Because of these advantages, a material of the foregoing composition is also applicable in the present invention.

By adding a trace of $Fe_2O_3$, $CeO_2$ or $MnO_2$ fine powder to fine powder of these materials, it is possible to reproduce a color tone close to that of natural teeth or ceramic teeth.

Addition of a slight amount of silica stone or kaolin fine powder permits improvement of bending strength of ceramics after firing. Fine powder of silica stone contributes to maintenance of a shape upon firing, and kaolin fine powder contributes to easier forming through an increased plasticity of fine powder of the materials.

A binder is uniformly dispersed in a material fine powder selected from among the foregoing ones, and the mixture is formed in a mold into an artificial tooth, an inlay, an onlay, a crown or a crown bridge or into a prescribed shape such as a block for CAD/CAM. Depending upon the material fine powder and/or the forming pressure, it is of course possible to form the material fine powder alone into a prescribed shape without using a binder.

Applicable binders include water, clay, phosphate, natural starch, protein, seaweeds (alginic acid), sugar, natural rubber, bitumen, and natural waste liquid (pulp, molasses), as well as a thermoplastic resin such as a polyethylene, a thermosetting resin such as epoxy and urethane, a synthetic rubber and a sublimate hydrocarbon (polycyclic compound), but are not limited to those enumerated above. One or more of these binders in mixture are used in response to the use. In order to uniformly disperse the binder in the material fine powder, it is necessary to use the binder in an appropriate liquid state. For a binder having a high liquid viscosity, being hard to be dispersed, the liquid viscosity of the binder must be reduced, and this is accomplished by diluting the binder with a solvent. Applicable solvents include alcoholic, ketone, ether and cycloalkane solvents. A mixed binder solution comprising a binder and a solvent is evaporated by firing, thus forming a porous ceramics having communicating holes.

After forming into a prescribed shape, the mixture is fired to obtain a porous ceramics. The firing temperature and the firing time vary with the material to be fired and the porosity permitting formation of communicating holes. The apparent porosity of this porous ceramics should preferably be within a range of from 0.5 to 70%. An apparent porosity of under 0.5% causes elasticity to disappear and makes it impossible to form communicating holes. An apparent porosity of over 70%, on the other hand, leads to an insufficient strength, thus making it difficult to keep a shape. An apparent porosity within a range of from 15 to 55% is preferable because it results in many communicating holes, a stable pore distribution and a sound balance of modulus of bending elasticity and bending strength.

Firing may be accomplished by any of vacuum firing and open-air firing, and firing causes fugacity of the binder through sublimation, evaporation or combustion, and sinters the fine powder.

For the purpose of obtaining the porous mass, it is also possible to treat a vitreous portion with a strong acid after firing to cause elution, thereby achieving a porous mass. For a large ceramic block, however, independent holes are easily formed, although communicating holes are hard to be formed, and the strong acid treatment requires a long period of time. This method is therefore applicable, although the foregoing method is preferable.

A coupling treatment should preferably be applied to the surfaces of the communicating holes of the foregoing porous ceramics with the use of a silane coupling agent, a titanate-based coupling agent, or a zircoaluminate-based coupling agent.

Applicable silane coupling agents include tetramethoxy silane, tetraethoxysilane, methyltrimethoxysilane, ethyltrimethoxysilane, phenyltrimethoxysilane, dimethyltrimethoxysilane, trimethylmethoxysilane, β-(metha)acryloyloxyethyltrimethoxysilane, γ-(metha)acryloyloxypropyltrimethoxysilane, γ-methacryloyloxypropyl-triethoxysilane, γ-methacryloyloxypropylmethyldimethoxysilane, vinyltrimethoxysilane, vinyltriethoxysilane, vinylmethyldimethoxy-silane, p -vinylphenyltrimethoxysilane, β-(3,4 epoxycyclohexyl)ethyltrimethoxysilane, γ-glycidyloxytrimethoxysilane, γ-aminopropyltrimethoxysilane, γ-aminopropyltriethoxysilane, N-phenyl-γ-aminopropyltrimethoxysilane, γ-glycidyloxytriethoxysilane, γ-chlorotrimethoxysilane, γ-mercaptopropyltrimethoxysilane, methyltrichlorosilane, and dimethyldichlorosilane.

Applicable titanate-based coupling agents include isopropyltriisostearoyltitanate, isopropyltridodecyl-benzenesulfonyltitanate, isopropyl-tris(dioctyl pyrophosphate)titanate, tetraisopropyl-bis(dioctyl phosphite)titanate, tetraoctyl-bis(di-tridecyl phosphite) titanate, tetra-(2,2-diallyloxymethyl-1-butyl)bis (ditridecyl)-phosphite titanate, bis(dioctyl pyrophosphate) oxyacetate titanate, bis(dioctyl pyrophosphate)-ethylene titanate, isopropyltrioctanoyltitanate, isopropyldimethacrylisostearoyl titanate, isopropyl-isostearoyldiacryl titanate, isopropyl tri(dioctyl phosphate)titanate, isopropyl tri-cumylphenyl titanate, isopropyl tri(N-aminoethyl-aminoethyl)titanate, dicumylphenyloxy acetate titanate, and di-iso-stearoylethylene titanate.

Applicable zircoaluminate-based coupling agents include alcoholic Cavco Mod and glycolic Cavco Mod.

These coupling agents are used singly or in combination of two or more. The reaction mechanism of coupling agents has not as yet been sufficiently clarified. When using a silane coupling agent from among those enumerated above, however, the alkoxy group ($CH_3O$) of the silane coupling agent is hydrolyzed by water serving as a solvent or water absorbed by the solvent, and leaving methanol becomes silanol group (SiOH). The thus formed silanol group is believed to enter into a condensation reaction and combine with the silanol group generated as a result of hydrolysis by water present on the porous ceramics surface. The methacyloyl group, on the other hand, improves adhesion with resin, and is desirable because of the improvement of bending strength and modulus of bending elasticity of the resin-impregnated ceramics.

A coupling agent can improve impregnating property and wettability of resin, and as compared with a case without coupling treatment, can assist penetration of the resin into fine holes of the porous ceramics, thus permitting reduction of the penetration time and achievement of a satisfactory impregnation. It is needless to mention that it is not always necessary to use a coupling agent.

The coupling agent is uniformly dispersed in a solvent to form a solution to cause the coupling agent to penetrate into the communicating holes of the porous ceramics.

A preferable diluting solvent of the silane coupling agent is one capable of dissolving silane alkoxyl at a low concentration and soluble in water, such as an alcohol and an ether. The silanol group dissolved in water is unstable and susceptible to a condensation reaction along with the lapse of time. It is therefore necessary to stably store the silane coupling agent and the solvent in the same dispersing condition as upon mixing the silane coupling agent and the solvent, and to cause a stable condensation reaction between the silane coupling agent and the porous ceramics surface. For this purpose, it is desirable to add an acidic component. Applicable acidic components to be added include acetic acid, phosphoric acid, formic acid, hydrochloric acid and sulfuric acid. Upon this addition, pH should be in the weak acidic region within a range of from 4.0 to 6.0 with a view to stabilizing the silane coupling agent in the solvent. When it is only a short period of time from mixing of the coupling agent to the treatment, it is not always necessary to adjust pH with an acidic component.

An alcohol or an ether may be used as a diluting solvent for a titanate-based coupling agent or a zircoaluminate-based coupling agent.

While there is no particular limitation on the consumption of the coupling agent, it should preferably be used in an amount, relative to 100 weight parts porous ceramics, within a range of from 0.1 to 200 weight parts, or more preferably, from 0.5 to 100 weight parts. The concentration of the coupling agent in the diluting solvent, not particularly limited, should preferably correspond to a low viscosity to ensure sufficient penetration into all portions of the communicating holes of the porous ceramics.

To ensure effective penetration of the solution of the coupling agent into all portions of the communicating holes of the porous ceramics and to cause a condensation reaction between the porous ceramics and the coupling agent, the porous ceramics should preferably be immersed into the coupling agent solution in ultrasonic wave and/or in a vacuum. The reaction temperature should preferably be within a range of from the room temperature to 120° C., and the reaction should usually be completed, depending upon the concentration of the solution, within 24 hours.

Applicable resins to impregnate the porous ceramics include thermoplastic resins such as vinyl acetate, vinyl chloride, vinylidene chloride, ester (metha)acrylate, vinyl propionate, butylene, propylene, acrylonitrile, and styrene, and thermosetting resins such as melamine, phenol, epoxy and urethane, used in combination of two or more of the above within the respective systems. From among these resins, preferable are polymerizable compounds containing at least one ethylene double bond, which have a low viscosity, are hard to soften or swell after polymerization, satisfactory in water resistance, alkali resistance and chemical resistance, require only a short period of time for polymerization, and are excellent in adhesion with a denture base, a support or natural teeth through an adhesive after forming into an artificial tooth, an inlay, an onlay, a crown or a crown bridge.

Applicable compounds having one ethylenic double bond include methyl(metha)acrylate, ethyl(metha)acrylate, isopropyl(metha)acrylate, 2-hydroxyethyl(metha)acrylate, n-butyl(metha)acrylate, i-butyl(metha)acrylate, t-butyl (metha)acrylate, 2-hydroxypropyl(metha)acrylate, tetrahydrofurfuryl(metha)acrylate, glycidyl(metha)acrylate, 2-methoxyethyl(metha)acrylate, 2-ethylhexyl(metha) acrylate, benzyl(metha)acrylate, trifluoroethyl(metha) acrylate, heptadecafluorodecyl(metha)acrylate, diethylaminoethyl(metha)acrylate, dimethylaminoethyl (metha)-acrylate, lauryl(metha)acrylate, tridecyl(metha) acrylate, stearyl(metha)acrylate, alkyl(metha)acrylate, cyclohexyl(metha)acrylate, aryl(metha)acrylate, methoxydi-ethyleneglycol(metha)acrylate, and methoxypolyethylene-glycol(metha)acrylate.

Applicable compound containing two ethylenic double bonds include ethyleneglycoldi(metha)acrylate, diethyleneglycoldi(metha)acrylate, triethyleneglycoldi(metha)acrylate, neopentylglycoldi(metha)acrylate, 1,3-butanedioldi(metha)acrylate, 1,4-butanedioldi(metha) acrylate, 1,6-hexane-dioldi(metha)acrylate, 2,2-bis(4-(metha)acryloxypoly-ethoxyphenyl)propane, 2,2-bis(4-(metha)acryloxypoly-propoxyphenyl)propane, bis(4-(metha)acryloxypolyethoxy-phenyl)methane, 2,2-bis(4-(metha)acryloxydiethoxy-phenyl)propane, bis(metha)acryloxyethylhydroxyiso-cynaulate, 2,6-bis[2'-(metha)acryloxyethyl]methyl urethane capronate, 2,2-bis[p -(2-(metha)acryloxyalkyleneoxy) phenyl]propane, 3,9-bis(2-(metha)acryloxy-1,1-dimehtylethyl)-2,4,8,10-tetra-oxaspiro [5,5]undecane, and pentaerythritoltetra(metha)acrylate. (Metha)acrylate compounds having an urethane bond such as di-2-(metha)acryloxyethyl-2,2,4-trimethylhexamethylenedi-carbamate may of course be adopted.

Applicable compounds having three ethylenic double bonds include trimethylolpropanetri(metha)acrylate, trimethylol-ethanetri(metha)acrylate, pentaerythritoltri (metha)acrylate and trimethylolmethanetri(metha)acrylate.

Applicable compounds having four or more ethylenic double bonds include 1,3,5-tris[1,3-bis(metha)acryloyloxy) -2-propoxycarbonylaminohexane]-1, 3,5-(1H, 3H, 5H)triazine-2,4,6-trion.

These compounds for resin may be used singly or in combination of two or more of liquid monomer and/or oligomer, and the combination and the blending ratio may appropriately be selected in response to the use such as an artificial tooth, an inlay, an onlay, a crown or a crown bridge.

These compounds for resin are polymerized with the use of a polymerizing catalyst. Applicable polymerizing catalysts include a thermo-polymerization initiator, a chemical polymerization initiator and a photo-polymerization initiator singly or in combination of two or more.

Applicable thermo-polymerization initiators include peroxides such as benzoylperoxide, ketone peroxide, peroxyketal, hydroperoxide, dialkylperoxide, diacylperoxide, peroxyester and peroxycarbonate, and azo-based compounds such as 2,2-azobisisobutylonitrile, 2,2-azobis 2-methylbutylonitrile, 2,2-azobis 2-methylheptonitrile, 1,1-azobis 1-cyclohexanecarbonitrile, dimethyl-2,2-azobisisobutylate, 2,2-azobis-(2-aminopropane)dihydride, 2,2-azobis(2-methylbutylonitrile), 4,4-azobis-4-cyano valeric acid and 2,2-azobis-2,4-dimethylvaleronitrile.

Applicable chemical polymerization initiators include a combination of a peroxide and a grade 3 amine or an organic metal compound, and a combination of a pyrimidine-trionic acid derivative and grade 4 ammonium chloride.

A combination of a sensitizer and a reducing agent is usually used as a photo-polymerization initiator. Applicable sensitizers include camphor quinone, benzyl diacetyl, benzyldimethylketal, benzyldiethylketal, benzyldi(2-methoxyethyl)ketal, 4,4-dimethylbenzylmethylketal, anthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthio-xanthone, thioxanthone-10, 10-dioxyd, thioxanthone-10-oxide, benzoinmethylether, benzoinethylether, isopropyl-ether, benzoinisobutylether, benzophenone, bis(4-dimethylaminophenone)ketone, 4,4-bisdiethylaminobenzo-phenone, and compounds containing an acido group, used singly or with two or more in combination. The compound and the ratio thereof are arbitrarily selected in response to the use.

A grade 3 amine or the like is usually used as a reducing agent. As the grade 3 amine, there is adopted any of dimethylaminoethylmethacrylate, triethanolamine, 4-dimethylamino methyl benzoate, 4-dimethylamino ethyl benzoate, and 4-dimethylamino isoamyl benzoate. Apart from these, benzoylperoxide, organic metal compounds and sulfinic acid derivatives are also applicable.

When using a photo-polymerization type initiator singly or with two or more in combination, a polymerization reaction is accomplished by irradiating an active light such as ultraviolet rays or a visible light. Applicable light sources include various mercury lamps of ultra-high, high, medium and low voltage, a chemical lamp, a carbon-arc lamp, a metal halide lamp, a fluorescent lamp, a tungsten lamp, a xenon lamp, an argon ion laser and the like.

The amount of added polymerization initiator should be appropriately selected within a range of from 0.001 to 20 wt. % in response to the ability of the initiator.

A monomer and/or oligomer containing any of these polymerization catalysts in a liquid state are caused to penetrate into communicating holes of the porous ceramics. Penetration should preferably be carried out in ultrasonic wave and/or in a vacuum. After penetration, the monomer and/or oligomer containing the polymerization catalyst are polymerized in a tightly closed vessel under any condition selected from among the room temperature and atmospheric pressure, the room temperature and pressurizing, heating and pressurizing, and heating and atmospheric pressure, thereby obtaining a resin-impregnated composite material.

A colorant, a polymerization inhibitor, an oxidation stabilizer, an ultraviolet-ray absorbing agent, a pigment or a dye may as required be added to the compound solution.

The dental material of the present invention can be manufactured for example as follows.

Assume now that a porous ceramics is silane-coupling-treated.

Figure 1:
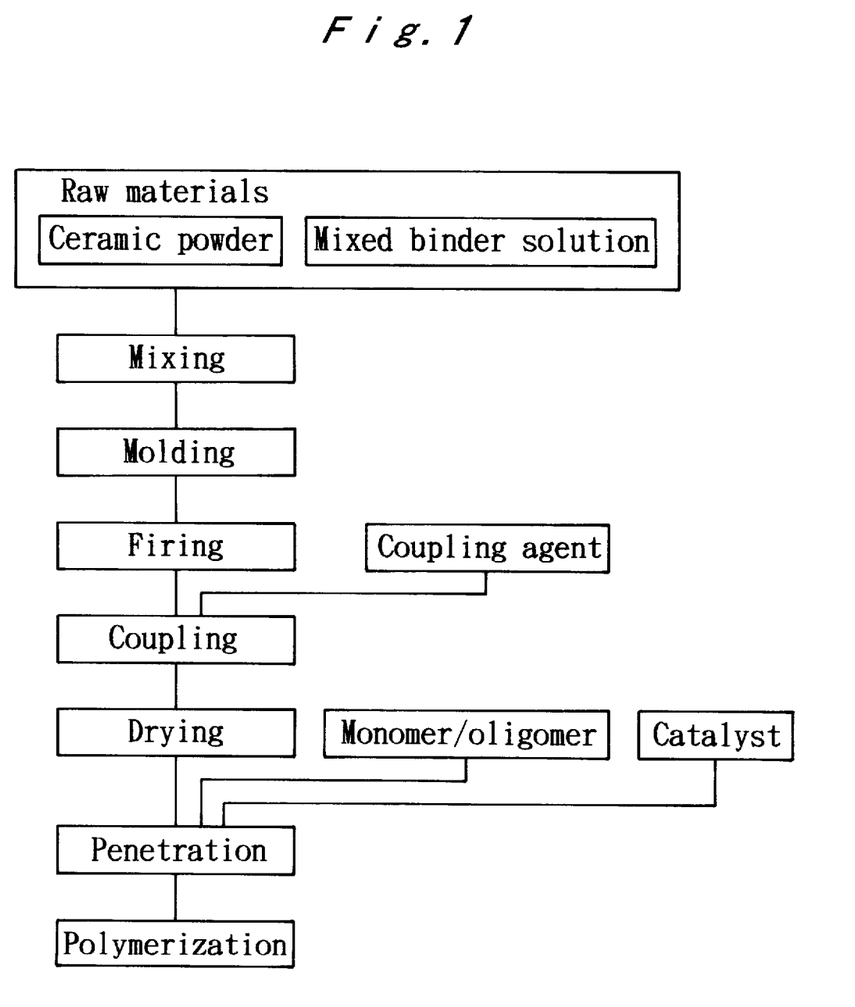
FIG. 1 is a process diagram illustrating an embodiment of the method of manufacturing the dental material of the present invention.

As shown in FIG. 1, the manufacturing method of the present invention comprises the steps of: (a) mixing raw materials including ceramic fine powder having adjusted particle sizes and a binder (mixing step); then (b) forming the mixture into a prescribed shape by means of a mold (molding step); (c) taking out the formed mixture from the mold, vacuum-sintering in a furnace to evaporate the binder at a prescribed temperature, thereby obtaining a porous ceramics having communicating holes (firing step); (d) immersing the resultant porous ceramics in a solution containing a dispersed silane coupling agent to cause the silane coupling agent to penetrate into the communicating holes of the porous ceramics in a tightly closed vessel in ultrasonic wave and/or in a vacuum for coupling treatment (coupling treatment step); (e) drying the coupling-treated porous ceramics (drying step); then (f) immersing the coupling-treated porous ceramics in a mixed solution comprising a monomer and/or oligomer and a polymerization initiator, reducing pressure in the tightly closed vessel to cause the mixed solution to penetrate into the communicating holes of the coupling-treated porous ceramics (penetration step); and (g) taking out the porous ceramics from the mixed solution and polymerizing the monomer and/or oligomer (polymerization step), thereby obtaining a resin-impregnated product.

EXAMPLES (Example 1)
<Adjustment of raw materials of porous ceramics>

A ceramics was manufactured by melting an aluminosilicate ceramics comprising 67 weight parts $SiO_2$ as a network-forming oxide, 20 weight parts $Al_2O_3$ as an intermediate oxide, 6 weight parts $K_2O$ as a network-modifying oxide and 6 weight parts $Na_2O$, and containing trace of MgO, CaO, $Fe_2O_3$, $TiO_2$, silica stone and kaolin. The resultant ceramics was milled on a ball mill, and the thus obtained coarse powder was sieved, thereby obtaining a ceramics powder having an average particle size of 7 $\mu$m and particle sizes within a range of from 0.5 to 40 $\mu$m. A mixed binder solution comprising 50 weight parts sublimate hydrocarbon compound and 50 weight parts cyclohexane serving as a solvent was used as a binder. Relative to 100 weight parts ceramics powder, 40 weight parts mixed binder solution was mixed with the ceramics powder while stirring and adding cyclohexane so as to ensure uniform mixing of the ceramics powder and the mixed binder solution. Then, cyclohexane was evaporated at the room temperature, thus obtaining a mixed powder.

<Firing of porous ceramics>

The resultant mixed powder was formed in a mold for block for CAD/CAM. The formed block was fired in a vacuum firing furnace in a vacuum of about 50 HPa at 1,040° C. for ten minutes, thereby obtaining a porous ceramics block having an apparent porosity of 35%. The apparent porosity was measured by a method as described later.

<Coupling treatment>

The porous ceramics block in an amount of 10 weight parts was immersed in an ethanol solvent containing 1 weight part γ-methacryloxypropyltrimethoxysilane, and ultrasonic wave was caused to act for 60 minutes to ensure penetration of the treatment solution into all portions of the communicating holes. Then, the porous ceramics block was taken out from the coupling treatment solution, and held at 100° C. for one hour to cause evaporation of ethylalcohol and excess water. The block is then subjected to a coupling treatment at 120° C. for two hours, thus obtaining a coupling-treated porous ceramics block.

<Penetration and polymerization of resin>

A mixed solution was prepared, which comprised 39 weight parts compound I, 15 weight parts compound II, 30 weight parts NPG, 16 weight parts compound IV, and 0.5 weight parts azo-catalyst M. The foregoing coupling-treated porous ceramics block was immersed in this mixed solution, and ultrasonic was applied thereto to cause penetration of the mixed solution into all portions of the communicating holes.

Then, the block was polymerized at the room temperature under the atmospheric pressure, thereby obtaining a resin-impregnated ceramics.

In this example, the compound I means di-2-methacryloxy-ethyl-2,2,4-trimethylhexamethylenedicarbamate; the compound II, 1,3,5-tris[1,3-bis(methacryloxy)-2-propoxycarbonyl-aminohexane]-1, 3,5-(1H, 3H, 5H) triadine-2,4,6-trion; NPG, neopentylglycol; the compound IV, trifluoroethyl-methacrylate; and the azo-catalyst M, 2,2-azobis(2-methyl-butylonitrile).

The thus obtained resin-impregnated ceramics was cut into pieces having dimensions of 6.5×2.0×24 mm. The surface was buffed with titanium oxide, and the pieces were immersed in water for a day to serve as test pieces. These test pieces were subjected to tests of physical properties (bending strength, modulus of bending elasticity, impact strength, wear rate) and change in color tone (coloring resistance, color fastness) in accordance with the test methods as described below. The results are as shown in Table 1.

1) The condition of impregnation was determined by observing the test piece with the naked eye: absence of color irregularities was marked good, and presence thereof was marked poor.

2) Bending strength and modulus of bending elasticity were measured through a test carried out by the use of an autograph (made by Shimazu Company) with a cross-head speed of 1 mm/min and a gauge length of 20 mm.

3) Impact strength was measured by means of a dyne stud impact tester (made by Tokyo Seiki Company) with an energy of 2.5 kg·cm, using a copper rod having a diameter of 6 mm for the impact section.

4) Wear resistance was determined by the use of a wear tester (made by Tokyo Giken Company) and a hard resin (G.C. Duradent foreteeth) as the wear resistant material, by measuring the wear after 100,000 runs of impact.

5) Coloring resistance was determined by immersing for 60 minutes a test piece in a boiling aqueous basic Fuchsine solution having a concentration of 0.2% at 100° C. and observing with the naked eye a color difference between a piece not as yet tested and a tested piece. A slight color difference was represented by a mark 3, the presence of a color difference, 2, and a considerable difference, 1.

6) Color fastness was determined by using a prototype thermal cycle tester, repeating alternate immersion of a test piece in cold water at 4° C. and in hot water at 60° C. every 30 seconds, and observing with the naked eye a color difference between a tested piece after 2,000 cycles and a piece not as yet tested. A slight color difference was represented by a mark 3, the presence of a color difference, 2, and a considerable difference, 1.

Apparent porosity was measured by the following method.

The method comprised the steps of immersing the porous ceramics block in water, keeping the block in water in a vacuum until complete elimination of bubbles, causing water to penetrate into all portions of the communicating holes under the action of ultrasonic wave for 60 minutes, then after action of ultrasonic wave, taking out the block from water, holding the block for 24 hours, measuring the weight thereof in water (weight A), wiping off excess water depositing onto the surface, measuring the dry-surface weight (weight B), then drying the block in a dryer, measuring the weight in dry (weight C), and calculating apparent porosity from weights A, B and C in accordance with the following formula:

Apparent porosity (%)=(B−C)/(B−A)×100

(Examples 2 and 3)

A resin-impregnated ceramics was prepared in the same manner as in the Example 1 except that the amount of the mixed binder solution was changed to 30 weight parts or 25 weight parts relative to 100 weight parts ceramics powder, and the same tests as in the Example 1 were carried out. The results are shown in the columns for the Examples 2 and 3 in Table 1.

(Example 4)

A resin-impregnated ceramics was prepared in the same manner as in the Example 1 except that 0.5 weight parts benzoyl peroxide (B.P.O.) were used in place of the azo-catalyst M, and the same tests as in the Example 1 were carried out. The results are shown in the column for the Example 4 in Table 1.

(Example 5)

A resin-impregnated ceramics was prepared in the same manner as in the Example 1 except that 43 weight parts compound I, 10 weight parts compound II, 35 weight parts NPG, and 12 weight parts compound IV were used, and the same tests as in the Example 1 were carried out. The results are shown in the column of the Example 5 in Table 1.

TABLE 1

|  |  | Example 1 | Example 2 | Example 3 | Example 4 | Example 5 |
| --- | --- | --- | --- | --- | --- | --- |
| Ceramic powder | $SiO_2$ | 67 | 67 | 67 | 67 | 67 |
|  | $Al_2O_3$ | 20 | 20 | 20 | 20 | 20 |
|  | $K_2O$ | 6 | 6 | 6 | 6 | 6 |
|  | $Na_2O$ | 6 | 6 | 6 | 6 | 6 |
|  | CaO | Trace | Trace | Trace | Trace | Trace |
|  | MgO | Trace | Trace | Trace | Trace | Trace |
|  | $TiO_2$ | Trace | Trace | Trace | Trace | Trace |
|  | $Fe_2O_3$ | Trace | Trace | Trace | Trace | Trace |
|  | Silica stone | Trace | Trace | Trace | Trace | Trace |
|  | Kaolin | Trace | Trace | Trace | Trace | Trace |
| Mixed powder | Ceramic powder | 100 | 100 | 100 | 100 | 100 |
|  | Mixed binder solution | 40 | 30 | 25 | 40 | 40 |
| Apparent porosity (%) |  | 35 | 35 | 35 | 35 | 35 |
| Surface treatment | Treatment | Applied | Applied | Applied | Applied | Applied |
|  | Drying time (hr) | 2 | 2 | 2 | 2 | 2 |
| Mixed Solution | Compound I | 39 | 39 | 39 | 39 | 43 |
|  | Compound II | 15 | 15 | 15 | 15 | 10 |
|  | Compound III | — | — | — | — | — |
|  | NPG | 30 | 30 | 30 | 30 | 35 |
|  | Compound IV | 16 | 16 | 16 | 16 | 12 |
|  | MMA | — | — | — | — | — |
|  | Compound V | — | — | — | — | — |
|  | Azo-catalyst M | 0.5 | 0.5 | 0.5 | — | 0.5 |
|  | B.P.O | — | — | — | 0.5 | — |
| Impregnating condition |  | Good | Good | Good | Good | Good |
| Physical properties | Bending strength (MPa) | 126 | 124 | 124 | 128 | 121 |
|  | Modulus of bending elasticity (MPa) | 15260 | 17820 | 20950 | 15800 | 15380 |
|  | Impact strength | 2.5 | 2.3 | 2.1 | 2.5 | 2.4 |
|  | Wear (μm) | 0.2 | 0.2 | 0.3 | 0.2 | 0.3 |
| Change in color tone | Coloring resistance | 3 | 3 | 3 | 3 | 3 |
|  | Color fastness | 3 | 3 | 3 | 3 | 3 |

Impact strength: unit (kgf · cm/cm$^2$)

(Example 6)

A resin-impregnated ceramics was prepared in the same manner as in the Example 1 except that 43 weight parts compound I, 10 weight parts 2,2-bis[4-(2-hydroxy-3-methacryloxypropoxy)phenyl]propane (compound III), an aromatic polyfunctional monomer, in place of the compound II, 35 weight parts NPG and 12 weight parts compound IV were used, and the same tests as in the Example 1 were carried out. The results are shown in the column of the Example 6 in Table 2.

(Example 7)

A resin-impregnated ceramics was prepared in the same manner as in the Example 1 except that 50 weight parts compound I, 20 weight parts NPG, 10 weight parts compound IV, and 20 weight parts methylmethacrylate (MMA) in place of the compound II, and the same tests as in the Example 1 were carried out. The results are shown in the column for the Example 7 in Table 2.

(Example 8)

A mixed powder prepared by mixing 100 weight parts ceramics powder (average particle size: 7 μm, particle size: from 0.5 to 40 μm) having a chemical composition shown in the column of the Example 8 in Table 2 and 40 weight parts the same mixed binder solution as in the Example 1 was formed in the same mold as in the Example 1, and fired at 1,100° C. for ten minutes in a vacuum of 50 HPa, thereby obtaining a porous ceramics block having an apparent porosity of 35%. After carrying out a coupling treatment in the same manner as in the Example 1, the porous ceramics block was immersed in a mixed solution of a blending ratio shown in the column of the Example 8 in Table 2, and ultrasonic wave was caused to act thereon for three hours. Then; polymerization was conducted at the room temperature under the atmospheric pressure in the same manner as in the Example 1, thereby obtaining a resin-impregnated ceramics. The thus obtained resin-impregnated ceramics was subjected to the same tests as in the Example 1. The results are as shown in the column of the Example 8 in Table 2.

(Example 9)

The same mixed powder as in the Example 8 was formed in the same mold as in the Example 1, and fired at 1,100° C. for ten minutes in a vacuum of 50 HPa, thereby obtaining a porous ceramics block having an apparent porosity of 35%. After carrying out a coupling treatment in the same manner as in the Example 1, the coupling-treated porous ceramics block was immersed in a mixed solution of the blending ratio shown in the column of the Example 9 in Table 2, and ultrasonic wave was caused to act for three hours. Then, polymerization was conducted at the room temperature and under the atmospheric pressure in the same manner as in the Example 1, thereby obtaining a resin-impregnated ceramics. The thus obtained resin-impregnated ceramics was subjected to the same tests as in the Example 1. The results are as shown in the column of the Example 9 in Table 2.

TABLE 2

|  |  | Example 6 | Example 7 | Example 8 | Example 9 |
|---|---|---|---|---|---|
| Ceramic powder | $SiO_2$ | 67 | 67 | 72 | 72 |
|  | $Al_2O_3$ | 20 | 20 | 14 | 14 |
|  | $K_2O$ | 6 | 6 | 10 | 10 |
|  | $Na_2O$ | 6 | 6 | 3 | 3 |
|  | CaO | Trace | Trace | Trace | Trace |
|  | MgO | Trace | Trace | Trace | Trace |
|  | $TiO_2$ | Trace | Trace | Trace | Trace |
|  | $Fe_2O_3$ | Trace | Trace | Trace | Trace |
|  | Silica stone | Trace | Trace | Trace | Trace |
|  | Kaolin | Trace | Trace | Trace | Trace |
| Mixed powder | Ceramic powder | 100 | 100 | 100 | 100 |
|  | Mixed binder solution | 40 | 40 | 40 | 40 |
| Apparent porosity (%) |  | 35 | 35 | 35 | 35 |
| Surface treatment | Treatment | Applied | Applied | Applied | Applied |
|  | Drying time (hr) | 2 | 2 | 2 | 2 |
| Mixed Solution | Compound I | 43 | 50 | 47 | 10 |
|  | Compound II | — | — | 5 | — |
|  | Compound III | 10 | — | — | — |
|  | NPG | 35 | 20 | 35 | 20 |
|  | Compound IV | 12 | 10 | 13 | — |
|  | MMA | — | 20 | — | 60 |
|  | Compound V | — | — | — | 10 |
|  | Azo-catalyst M | 0.5 | 0.5 | 0.5 | 0.5 |
|  | B.P.O | — | — | — | — |
| Impregnating condition |  | Good | Good | Good | Good |
| Physical properties | Bending strength (MPa) | 122 | 114 | 117 | 110 |
|  | Modulus of bending elasticity (MPa) | 14970 | 14240 | 15010 | 14000 |
|  | Impact strength | 2.3 | 2.5 | 2.4 | 2.6 |
|  | Wear (μm) | 0.2 | 0.4 | 0.4 | 0.6 |
| Change in color tone | Coloring resistance | 2 | 3 | 3 | 2 |
|  | Color fastness | 2 | 3 | 3 | 2 |

Impact strength: unit (kgf · cm/cm$^2$)

(Example 10)

As shown in the column of the Example 10 in Table 3, a ceramics was prepared by melting an alumino-silicate ceramics comprising 88 weight parts feldspar, trace $SiO_2$ as a network-forming oxide, 5 weight parts $Al_2O_3$ as an intermediate oxide, and 10 weight parts $K_2O$ as a network-modifying oxide, added with trace $Na_2O$, $TiO_2$, CaO and MgO. The resultant ceramics was milled on a ball mill, and the produced coarse powder was sieved to obtain a ceramics powder having an average particle size of 40 μm and particle sizes of up to 120 μm. By using 100 weight parts ceramics powder thus obtained, mixed with 40 weight parts mixed binder solution identical with that used in the Example 1, the mixture was formed in the same mold as in the Example 1, fired at 770° C. for ten minutes in a vacuum of 50 HPa, thus resulting in a porous ceramics block having an apparent porosity of 33%. After carrying out a coupling treatment in the same manner as in the Example 1, the porous ceramics block was immersed in a mixed solution having the blending ratio shown in the column of the Example 9 in Table 2, and ultrasonic wave was applied for three hours. Then, polymerization was conducted at the room temperature under the atmospheric pressure in the same manner as in the Example 1, thereby obtaining a resin-impregnated ceramics. The same tests as in the Example 1 were carried out on the resultant resin-impregnated ceramics. The results are as shown in the column of the Example 10 in Table 3.

(Example 11)

The ceramics obtained in the Example 10 as shown in Table 3 was heat-treated at 700° C., to cause precipitation of crystal grains. This was milled on a ball mill, thus obtaining a coarse powder. The coarse powder was sieved to obtain a ceramics powder having an average particle size of 40 μm and particle sizes of up to 120 μm. A mixed powder of this ceramics powder in an amount of 100 weight parts mixed with 40 weight parts the same mixed binder solution as in the Example 1 was formed in the same mold as in the Example 1, fired at 770° C. for ten minutes in a vacuum of 50 HPa, thereby obtaining a porous ceramics block having an apparent porosity of 30%. After carrying out a coupling treatment in the same manner as in the Example 1, the porous ceramics block was immersed in a mixed solution having the blending ratio shown in the column of the Example 9 in Table 2, and ultrasonic wave was applied for three hours. Then, polymerization was conducted at the room temperature under the atmospheric pressure in the same manner as in the Example 1, thereby obtaining a resin-impregnated ceramics. The same tests as in the Example 1 were carried out on the resultant resin-impregnated ceramics. The results are as shown in the column of the Example 11 in Table 3.

TABLE 3

|  |  | Example 10 | Example 11 |
|---|---|---|---|
| Ceramic powder | Felspar | 88 | 88 |
|  | SiO$_2$ | Trace | Trace |
|  | Al$_2$O$_3$ | 5 | 5 |
|  | K$_2$O | 10 | 10 |
|  | Na$_2$O | Trace | Trace |
|  | CaO | Trace | Trace |
|  | MgO | Trace | Trace |
|  | TiO$_2$ | Trace | Trace |
| Mixed powder | Ceramic powder | 100 | 100 |
|  | Mixed binder solution | 40 | 40 |
| Apparent porosity (%) |  | 33 | 30 |
| Surface treatment | Treatment | Applied | Applied |
|  | Drying time (hr) | 2 | 2 |
| Mixed Solution | Compound I | 10 | 10 |
|  | Compound II | — | — |
|  | Compound III | — | — |
|  | NPG | 20 | 20 |
|  | Compound IV | — | — |
|  | MMA | 60 | 60 |
|  | Compound V | 10 | 10 |
|  | Azo-catalyst M | 0.5 | 0.5 |
|  | B.P.O | — | — |
| Impregnating condition |  | Good | Good |
| Physical properties | Bending strength (MPa) | 120 | 129 |
|  | Modulus of bending elasticity (MPa) | 13980 | 15130 |
|  | Impact strength | 2.4 | 2.6 |
|  | Wear (μm) | 0.6 | 0.6 |

TABLE 3-continued

|  |  | Example 10 | Example 11 |
|---|---|---|---|
| Change in color tone | Coloring resistance | 2 | 2 |
|  | Color fastness | 2 | 2 |

Impact strength: unit (kgf · cm/cm$^2$)

(Comparative Example 1)

The ceramics powder alone in the Example 1 was used. The ceramics powder was fired at 1,300° C. for 15 minutes to achieve a molten state, thereby eliminating pores. The resultant ceramics was subjected to the same tests as in the Example 1. The results as shown in the column of the Comparative Example 1 in Table 4 demonstrate a large modulus of bending elasticity, a brittle material poor in impact strength, and a far inferior bending strength to that in the Examples.

(Comparative Example 2)

The porous ceramics block obtained in the Example 1 was subjected to a coupling treatment alone, and then, to the same tests as in the Example 1. The results are shown in the column of Comparative Example 2 in Table 4. This porous-ceramics block, having a satisfactory modulus of bending elasticity, was very low in bending strength and impact strength, and completely wore out in the wear resistance test. This is attributable to the weak bond between ceramics particles and the partial bond. The block was inferior also in coloring resistance and color fastness.

(Comparative Example 3)

The porous ceramics block obtained in the Example 1 was subjected to a coupling treatment in the same manner as in the Example 1, and impregnated with the same mixed solution as in the Example 1 without using ultrasonic wave and polymerized. The immersion time and the polymerization conditions were the same as in the Example 1, with however an insufficient penetration of the mixed solution and impregnation of only the surface. The resultant composite ceramics material was subjected to the same tests as in the Example 1. The results are as shown in the column of the Comparative Example 3 in Table 4. The thus obtained composite ceramics showed a bending strength inferior to that in the Example 1.

(Comparative Example 4)

The same mixed powder as in the Example 1 was fired at 1,180° C. for ten minutes in a vacuum of 50 HPa, thereby obtaining a ceramics block. From the resultant ceramics block, a composite ceramics material was obtained in the same manner as in the Example 1 except that the same mixed solution as in the Example 4 was used, and subjected to the same tests as in the Example 1. The results are as shown in the column of the Comparative Example 4 in Table 4. Because of a smaller apparent porosity as compared with the Example 1, the block showed a larger modulus of bending elasticity, was brittle and poor in impact strength. It is inferior to the Example 1 even in bending strength.

TABLE 4

|  |  | Comparative example 1 | Comparative example 2 | Comparative example 3 | Comparative example 4 |
|---|---|---|---|---|---|
| Ceramic powder | SiO$_2$ | 67 | 67 | 67 | 67 |
|  | Al$_2$O$_3$ | 20 | 20 | 20 | 20 |
|  | K$_2$O | 6 | 6 | 6 | 6 |
|  | Na$_2$O | 6 | 6 | 6 | 6 |

TABLE 4-continued

|  |  | Comparative example 1 | Comparative example 2 | Comparative example 3 | Comparative example 4 |
|---|---|---|---|---|---|
|  | CaO | Trace | Trace | Trace | Trace |
|  | MgO | Trace | Trace | Trace | Trace |
|  | $TiO_2$ | Trace | Trace | Trace | Trace |
|  | $Fe_2O_3$ | Trace | Trace | Trace | Trace |
|  | Silica stone | Trace | Trace | Trace | Trace |
|  | Kaolin | Trace | Trace | Trace | Trace |
| Mixed powder | Ceramic powder | 100 | 100 | 100 | 100 |
|  | Mixed binder solution | 0 | 40 | 40 | 40 |
| Apparent porosity (%) |  | 0 | 35 | 35 | 0.1 |
| Surface treatment | Treatment | Not applied | Applied | Applied | Applied |
|  | Drying time (hr) | — | 2 | 2 | 2 |
| Mixed Solution | Compound I | — | — | 39 | 39 |
|  | Compound II | — | — | 15 | 15 |
|  | Compound III | — | — | — | — |
|  | NPG | — | — | 30 | 30 |
|  | Compound IV | — | — | 16 | 16 |
|  | MMA | — | — | — | — |
|  | Compound V | — | — | — | — |
|  | Azo-catalyst M | — | — | 0.5 | — |
|  | B.P.O | — | — | — | 0.5 |
| Impregnating condition |  | — | — | Poor | Poor |
| Physical properties | Bending strength (MPa) | 72 | 11 | 46 | 70 |
|  | Modulus of bending elasticity (MPa) | 40520 | 11350 | 15940 | 37000 |
|  | Impact strength | — | 0.1 | 2.1 | — |
|  | Wear (μm) | 0 | — | 0.3 | 0.2 |
| Change in color tone | Coloring resistance | 3 | 1 | 1 | 2 |
|  | Color fastness | 3 | 1 | 1 | 2 |

Impact strength: unit (kgf · cm/cm$^2$2)

According to the present invention, there is provided a dental material which can keep mechanical strength such as wear resistance and bending strength, color fastness, coloring resistance and aesthetic merit for a long period of time, because of the possibility of achieving a high filling ratio of inorganic materials by impregnating the communicating holes of the porous ceramics with resin, and is excellent in modulus of bending elasticity and impact strength, because of the alleviation of stress in the ceramics, and provided a dental material suitable for a CAD/CAM system.

According to the present invention, furthermore, it is possible to set mechanical strength such as wear resistance and bending strength, color fastness, coloring resistance, modulus of bending elasticity, impact strength and other properties to various levels by changing the raw material for ceramics, filling ratio and/or the kind of resin. It is therefore possible to provide easily and at a low cost a dental material having properties required by an artificial tooth, an inlay, an onlay, a crown and a crown bridge, or a block for CAD/CAM.

It is needless to mention that the present invention is not limited by the foregoing examples.

What is claimed is:

1. A dental material which comprises a porous ceramics block impregnated with a resin, said material being produced by a process which comprises:
   (a) molding into a prescribed shape a mixture comprising a ceramics powder having an average particle size within the range of from 3.0 to 50 μm and including a network-forming oxide, an intermediate oxide, a network-modifying oxide, and a binder,
   (b) firing the molded mixture to produce a porous ceramics block having communicating holes,
   (c) carrying out a coupling treatment on the surface of the communicating holes of said porous ceramics block by allowing at least one coupling agent selected from the group consisting of a silane coupling agent, a titanate coupling agent and a zircoaluminate coupling agent to penetrate the surface, in the presence of an ultrasonic wave and/or in a vacuum; and
   (d) allowing a monomer and/or an oligomer with at least an ethylenic double bond to penetrate into the communicating holes of the thus treated porous ceramics block in the presence of an ultrasonic wave and/or in a vacuum for subsequent polymerization therein therein.

2. A dental material according to claim 1, wherein the ceramics powder comprises the aluminosilicate combination $K_2O$—$Al_2O_3$—$SiO_2$ with $SiO_2$ constituting 40–80 weight %, $K_2O$ 1–30 weight % and $Al_2O_3$ 5–30 weight % of said combination.

3. A dental material according to claim 1, wherein the ceramics powder comprises the aluminosilicate combination $K_2O$—$Na_2O$—$Al_2O_3$—$SiO_2$ with $SiO_2$ constituting 40–80 weight %, $K_2O$ 1–30 weight %, $Na_2O$ 1–10 weight % and $Al_2O_3$ 5–30 weight % of said combination.

4. A dental material according to claim 1, wherein the ceramics powder comprises the borosilicate combination $Na_2O$—$B_2O_3$—$SiO_2$ with $SiO_2$ constituting 60–95 weight %, $Na_2O$ 0.1–10 weight % and $B_2O_3$ 1–30 weight % of said combination.

5. A dental material according to claim 1, wherein the ceramics powder comprises the aluminoborosilicate combination $Na_2O$—$Al_2O_3$—$B_2O_3$—$SiO_2$ with $SiO_2$ constituting 60–90 weight %, $Na_2O$ 0.1–15 weight %, $Al_2O_3$ 1–25 weight % and $B_2O_3$ 1–20 weight % of said combination.

6. A dental material according to claim 1 wherein said porous ceramics block has an apparent porosity within a range of from 0.5 to 70%.

7. A dental material according to claim 2, wherein said porous ceramics block has an apparent porosity within a range of from 0.5 to 70%.

8. A dental material according to claim 3 wherein said porous ceramics block has an apparent porosity within a range of from 0.5 to 70%.

9. A dental material according to claim 4 wherein said porous ceramics block has an apparent porosity within a range of from 0.5 to 70%.

10. A dental material according to claim 5 wherein said porous ceramics block has an apparent porosity within a range of from 0.5 to 70%.

11. A dental material which comprises a porous ceramics block impregnated with a resin, said material being produced by a process which comprises:
   (a) molding into a prescribed shape a mixture comprising 100 weight parts of a ceramic powders containing 67 weight parts of $SiO_2$, 20 weight parts of $Al_2O_3$, 6 weight parts of $K_2O$, and trace amounts of MgO, CaO, $Fe_2O_3$, $TiO_2$silica and kaolin and having an average particle size within a range of from 3.0 to 50 $\mu$m, and 12.5–20 weight parts of a sublimating hydrocarbon binder;
   (b) firing the molded mixture in a vacuum to produce a porous ceramics block having communicating holes and having an apparent porosity within the range of from 0.5 to 70%;
   (c) carrying out a coupling treatment on the surface of the communicating holes of said porous ceramics block by allowing at least one coupling agent selected from the group consisting of a silane coupling agent, a titanate coupling agent and a zircoaluminate coupling agent to penetrate the surface, in the presence of an ultrasonic wave and/or in a vacuum; and
   (d) allowing a monomer and/or an oligomer with at least an ethylenic double bond to penetrate into the communicating holes of the thus treated porous ceramics block in the presence of an ultrasonic wave and/or in a vacuum for subsequent polymerization therein therein.

12. A dental material which comprises a porous ceramics block impregnated with a resin, said material being produced by a process which comprises
   (a) molding into a prescribed shape a mixture comprising a ceramics powder containing, as main ingredients, feldspar, $Al_2O_3$, and $K_2O$, and trace amounts of $SiO_2$, $Na_2O$, CaO, MgO and $TiO_2$, and having an average particle size within a range of from 3.0 to 50 $\mu$m, and a sublimating hydrocarbon binder,
   (b) firing the molded mixture in a vacuum to produce a porous ceramics block having communicating holes and having an apparent porosity within the range of from 0.5 to 70%;
   (c) carrying out a coupling treatment on the surface of the communicating holes of said porous ceramics block by allowing at least one coupling agent selected from the group consisting of a silane coupling agent, a titanate coupling agent and a zircoaluminate coupling agent to penetrate the surface, in the presence of an ultrasonic wave and/or in a vacuum; and
   (d) allowing a monomer and/or an oligomer with at least an ethylenic double bond to penetrate into the communicating holes of thus treated porous ceramics block in the presence of an ultrasonic wave and/or in a vacuum for subsequent polymerization therein.

13. A dental material which comprises a porous ceramics block impregnated with a resin, said material being produced by a process which comprises:
   (a) molding into a prescribed shape a mixture comprising 100 weight parts of a ceramics powder containing 88 weight parts of feldspar, 5 weight parts of $Al_2O_3$, 10 weight parts of $K_2O$, and trace amounts of $SiO_2$, $Na_2O$, CaO, MgO and $TiO_2$, and having an average particle size within a range of from 3.0 to 50 $\mu$m, and 20 weight parts of a sublimating hydrocarbon binder,
   (b) firing the molded mixture in a vacuum to produce a porous ceramics block having communicating holes and having an apparent porosity within a range of from 0.5 to 70%;
   (c) carrying out a coupling treatment on the surface of the communicating holes of said porous ceramics block by allowing at least one coupling agent selected from the group consisting of a silane coupling agent, a titanate coupling agent and a zircoaluminate coupling agent to penetrate the surface, in the presence of an ultrasonic wave and/or in a vacuum; and
   (d) allowing a monomer and/or an oligomer with at least an ethylenic double bond to penetrate into the communicating holes of the thus treated porous ceramics block in the presence of an ultrasonic wave and/or in a vacuum for subsequent polymerization therein therein.

14. A method for manufacturing a dental material which comprises a porous ceramics block impregnated with a resin, said process comprising:
   (a) molding into a prescribed shape a mixture comprising a ceramics powder having an average particle size within a range of from 3.0 to 50 $\mu$m and including a network-forming oxide, an intermediate oxide, a network modifying oxide, and a binder,
   (b) firing the molded mixture to produce a porous ceramics block having communicating holes,
   (c) carrying out a coupling treatment on the surface of the communicating holes of said porous ceramics block by allowing at least one coupling agent selected from the group consisting of a silane coupling agent, a titanate coupling agent and a zircoaluminate coupling agent to penetrate the surface, in the presence of an ultrasonic wave and/or in a vacuum, and
   (d) allowing a monomer and/or an oligomer with at least an ethylenic double bond to penetrate into the communicating holes of the thus treated porous ceramics block in the presence of an ultrasonic wave and/or in a vacuum for subsequent polymerization therein therein.

15. A method according to claim 14 wherein the ceramics powder comprises the aluminosilicate combination $K_2O$—$Al_2O_3$—$SiO_2$ with $SiO_2$ constituting 40–80 weight %, $K_2O$ 1–30 weight % and $Al_2O_3$ 5–30 weight % of said combination.

16. A method according to claim 14 wherein the ceramics powder comprises the aluminosilicate combination $K_2O$—$Na_2O$—$Al_2O_3$—$SiO_2$ with $SiO_2$ constituting 40–80 weight %, $K_2O$ 1–30 weight % $Na_2O$ 1–10 weight % and $Al_2O_3$ 5–30 weight % of said combination.

17. A method according to claim 14 wherein the ceramics powder comprises the borosilicate combination $Na_2O$—$B_2O_3$—$SiO_2$ with $SiO_2$ constituting 60–95 weight %, $Na_2O$ 0.1–10 weight % and $B_2O_3$ 1–30 weight % of said combination.

18. A method according to claim 14 wherein the ceramics powder comprises the alumino-borosilicate combination $Na_2O$—$Al_2O_3$—$B_2O_3$—$SiO_2$ with $SiO_2$ constituting 60–90 weight %, $Na_2O$ 0.1–15 weight %, $Al_2O_3$ 1–25 weight % and $B_2O_3$ 1–20 weight % of said combination.

19. A method according to claim 14 wherein said porous ceramics block has an apparent porosity within the range of from 0.5 to 70%.

20. A method according to claim 15 wherein said porous ceramics block has an apparent porosity within a range of from 0.5 to 70%.

21. A method according to claim 16 wherein said porous ceramics block has an apparent porosity within a range of from 0.5 to 70%.

22. A method according to claim 17 wherein said porous ceramics block has an apparent porosity within a range of from 0.5 to 70%.

23. A method according to claim 18 wherein said porous ceramics block has an apparent porosity within a range of form 0.5 to 70%.

24. A method for manufacturing a dental material which comprises a porous ceramics block impregnated with a resin, said process comprising:
 (a) molding into a prescribed shape a mixture comprising 100 weight parts of a ceramics powder containing 67 weight parts of $SiO_2$, 20 weight parts of $Al_2O_3$, 6 weight parts of $K_2O$ and trace amounts of MgO, CaO, $Fe_2O_3$, $TiO_2$, silica and kaolin and having an average particle size within a range of from 3.0 to 50 $\mu$m, and 12.5–20 weight parts of a sublimating hydrocarbon binder,
 (b) firing the molded mixture in a vacuum to produce a porous ceramics block having communication holes and having an apparent porosity within a range of from 0.5 to 70%,
 (c) carrying out a coupling treatment on the surface of the communicating holes of said porous ceramics block by allowing at least one coupling agent selected from the group consisting of a silane coupling agent, a titanic coupling agent and a zircoaluminate coupling agent to penetrate the surface, in the presence of an ultrasonic wave and/or in a vacuum, and
 (d) allowing a monomer and/or an oligomer with at least an ethylenic double bond to penetrate into the communicating holes of the thus treated porous ceramics block in the presence of an ultrasonic wave and/or in a vacuum for subsequent polymerization therein therein.

25. A method for manufacturing a dental material which comprises a porous ceramics block impregnated with a resin, said process comprising:
 (a) molding into a prescribed shape a mixture comprising a ceramics powder containing, as main ingredients, feldspar, $Al_2O_3$, and $K_2O$, and trace amounts of $SiO_2$, $Na_2O$, CaO, MgO and $TiO_2$, and having an average particle size within a range of from 3.0 to 50$\mu$m, and a sublimating hydrocarbon binder,
 (b) firing the molded mixture in a vacuum to produce a porous ceramics block having communicating holes and having an apparent porosity within a range of from 0.5 to 70%,
 (c) carrying out a coupling treatment on the surface of the communicating holes of said porous ceramics block by allowing at least one coupling agent selected from the group consisting of a silane coupling agent, a titanate coupling agent and a zircoaluminate coupling agent to penetrate the surface, in the presence of an ultrasonic wave and/or in a vacuum, and
 (d) allowing a monomer and/or an oligomer with at least an ethylenic double bond to penetrate into the communicating holes of thus treated porous ceramics block in the presence of an ultrasonic wave and/or in a vacuum for subsequent polymerization therein therein.

26. A method for manufacturing a dental material which comprises a porous ceramics block impregnated with a resin, said process comprising:
 (a) molding into a prescribed shape a mixture comprising 100 weight parts of a ceramics powder containing 88 weight parts of feldspar, 5 weight parts of $Al_2O_3$, 10 weight parts of $K_2O$, and trace amounts of $SiO_2$, $Na_2O$, CaO, MgO and $TiO_2$, and having an average particle size within a range of from 3.0 to 50 $\mu$m, and 20 weight parts of a sublimating hydrocarbon binder,
 (b) firing the molded mixture in a vacuum to produce a porous ceramics block having communicating holes and having an apparent porosity within a range of from 0.5 to 70%,
 (c) carrying out a coupling treatment on the surface of the communicating holes of said porous ceramics block by allowing at least one coupling agent selected from the group consisting of a silane coupling agent, a titanate coupling agent and a zircoalumionate coupling agent to penetrate the surface, in the presence of an ultrasonic wave and/or in a vacuum, and
 (d) allowing a monomer and/or an oligomer with at least an ethylenic double bond to penetrate into the communicating holes of thus treated porous ceramics block in the presence of an ultrasonic wave and/or in a vacuum for subsequent polymerization therein therein.

* * * * *